US005707630A

United States Patent [19]
Morrow

[11] Patent Number: 5,707,630
[45] Date of Patent: Jan. 13, 1998

[54] HERBAL COMPOUND FOR RELIEF OF PMS THROUGH MENOPAUSAL SYMPTOMS

[75] Inventor: Tim Morrow, Hawthorne, Calif.

[73] Assignee: Sabina International, Ltd., Aspen, Colo.

[21] Appl. No.: 582,758

[22] Filed: Jan. 4, 1996

[51] Int. Cl.$^6$ .................................................. A61K 35/78
[52] U.S. Cl. ........................ 424/195.1; 424/464; 514/899
[58] Field of Search ..................... 424/195.1, 464; 514/899

[56] References Cited

U.S. PATENT DOCUMENTS

| | | | |
|---|---|---|---|
| 4,592,912 | 6/1986 | Nickolaus | 424/195.1 |
| 4,689,230 | 8/1987 | Ayoub | 424/195.1 |
| 5,565,199 | 10/1996 | Page et al. | 424/195.1 |
| 5,569,459 | 10/1996 | Shlyankevich | 424/195.1 |

OTHER PUBLICATIONS

Rebecca Flynn, *Your Nutritional Guide to Standardized Herbal Products*, published by Banyan Press, pp. 10–11, 26–27.

*100 Healing Herbs*, pp. 362–365.

David L. Hoffman, *Therapeutic Herbalism, A correspondence course in Phytotherapy*, pp. 5–39, 5–53–5–54, 5–92, 5–8, 5–17–5–19, 5–28–5–29, 5–27.

*CRC Handbook of Medicinal Herbs*, James A. Duke, Ph.D. author, CRC Press, Inc., pp. 98–99, 108, 317–318, 350, 403 (1985).

*British Herbal Compendium*, edited by Peter R. Bradley, British Herbal Medicine Association, pp. 52–53, 71–72, 112–113 (vol. 1).

Terry Willard, *The Wild Rose Scientific Herbal*, pp. 60–64, 104–105 (1991).

M. Grieve, *A Modern Herbal*, Dover Publications, Inc., p. 249 (vol. 1).

Alma R. Hutchens, et al., *Indian Herbalogy of North America*, p. 108.

Anaesthesia, "Forum: Ginger Root—a new antiemetic", vol. 45, Issue 8, pp. 669–671 (Aug. 1990).

Anaesthesia, "Ginger Root—a new antiemetic", vol. 45, Issue 12 (Dec. 1990).

Safety Data Sheet for Herbs, for Berry Leaves.

The Lawrence Review of Natural Products, Jun. 1986.

*The Toxicology of Botanical Medicines*, compiled by Francis J. Brinker, p. 26 (2nd Ed., 1983).

Nutrition Reviews, "Metabolism and Toxicity of Capsaicin", vol. 44, No. 1, pp. 20–22 (Jan. 1986).

Kooperation Phytopharmaka, Büro Bonn, der Verbände BAH, BPI, VHR und Gesellschaft für Phytotherapie.

Daniel B. Mowrey, *The Scientific Validation of Herbal Medicine*, p. 58 (1986).

*Primary Examiner*—John W. Rollins
*Attorney, Agent, or Firm*—Clifford L. Tager

[57] ABSTRACT

The present invention is directed to an herbal compound which aids in the relief of symptoms caused by female hormonal imbalances. The herbal compound of the present invention preferably comprises red raspberry, bayberry, blue cohosh, capsicum, cascara sagrada, damiana, ginger, valerian and a binding agent. The ratio of red raspberry to the other herbal constituents is preferably two to one. The herbal compound preferably further comprises a binding agent which comprises cellulose, to hold the herbal components together, as well as vegetable powder, used as a food carrier so that the herbal compound can be safely and effectively taken on an empty stomach. The binding agent preferably also comprises ingredients to allow the herbal compound to dissolve in the stomach. In the preferred embodiment, the herbal compound and binding agents are formed as a tablet, with the exterior surface thereof coated with a food glaze.

7 Claims, No Drawings

HERBAL COMPOUND FOR RELIEF OF PMS THROUGH MENOPAUSAL SYMPTOMS

BACKGROUND OF THE INVENTION

1. Technical Field

The present invention is directed to an herbal compound. More particularly, the present invention is directed to an herbal compound which aids in the relief of symptoms caused by female hormonal imbalances, such as those symptoms typically associated with pre- and post-menstrual cycle and menopause.

2. Background Information

The female body, from the commencement of menstruation until the termination of menopause, can experience wide fluctuations in baseline hormonal levels. When such fluctuations cause an imbalance in the hormonal composition, certain chemical reactions thereto present as symptoms which include headaches, cramping, nausea, inflammation, increased agitation, anxiety, tension, restlessness, decreased digestive tract activity, depression, moodiness and severe mood swings.

These symptoms, commonly referred to as PMS and/or menopausal symptoms, can be relieved. For example, additional hormones can be ingested to compensate for the specific hormones in which the body is deficient. Alternatively, substances can be introduced which offset and/or neutralize the chemical reactions which gave rise to the symptoms.

Given the changing characteristics of the hormonal imbalance during the menstrual cycle and/or menopause, as well as the variations in the specific hormonal imbalance from person to person, it would be advantageous to introduce a compound which adapts to meet the specific needs of each person, both over time as well as from person to person.

The human body is able to identify the chemical components in which it is deficient. An interesting and important feature of herbal interaction with the human body is the fact that the body will only absorb from an herbal compound those chemical components in which it is deficient. Those chemical components of the herbal compound which are not needed simply pass through the body without undue stress placed on the body.

SUMMARY OF THE INVENTION

The present invention is directed to an herbal compound which aids in the relief of symptoms caused by female hormonal imbalances. The herbal compound of the present invention preferably comprises red raspberry, bayberry, blue cohosh, capsicum, cascara sagrada, damiana, ginger, valerian, and a binding agent.

The ratio of red raspberry to the other herbal constituents is preferably two to one.

The herbal compound preferably further comprises a binding agent which comprises cellulose, to hold the herbal components together, as well as vegetable powder, used as a food carrier so that the herbal compound can be safely and effectively taken on an empty stomach. The binding agent preferably also comprises ingredients to allow the herbal compound to dissolve in the stomach, rather than in the intestine.

In the preferred embodiment, the herbal compound and binding agents are formed as a tablet, with the exterior thereof coated with a food glaze.

DESCRIPTION OF THE PREFERRED EMBODIMENT(S)

A great deal of pharmaceutical research has gone into analyzing the active ingredients of herbs to find out how and why they work. The effect which an herb has is commonly referred to as the herb's action. Herbal actions describe the ways in which the herb affects human physiology. The actions which make herbs beneficial in treating the human body include:

Adaptogenic: Adaptogenic herbs increase resistance and resilience when faced with stress, and work by supporting the adrenal glands.

Alternative: Herbs that gradually restore proper functioning of the body, increasing health and vitality.

Anti-inflammatory: Herbs that soothe inflammations or reduce the inflammatory response of the tissue directly.

Antimicrobial: Antimicrobials help the body destroy or resist pathogenic (disease causing) microorganisms.

Antispasmodic: Antispasmodics ease cramps in smooth and skeletal muscles. They alleviate muscular tension and can ease psychological tension as well.

Astringent: Astringents have a binding action on mucous membranes, skin and other tissue. They have the effect of reducing irritation and inflammation, and creating a barrier against infection that is helpful to wounds and burns.

Bitter: Herbs with a bitter taste have a special role in preventative medicine. The taste triggers a sensory response in the central nervous system leading to a range of responses, including stimulating appetite and the flow of digestive juices, aiding the liver's detoxification work, and increasing bile flow.

Carminative: Plants that are rich in aromatic volatile oils stimulate the digestive system. They soothe the gut wall, reduce inflammation, ease pain and help with the removal of gas from the digestive tract.

Demulcent: Demulcent herbs are rich in mucilage and soothe and protect irritated or inflamed tissue. They reduce irritation down the whole length of the bowel, reduce sensitivity to potentially corrosive gastric acids, help prevent diarrhea, and reduce the muscle spasms that cause colic.

Diuretic: Diuretics increase the production and elimination of urine.

Emmenagogue: Emmenagogues stimulate menstrual flow and activity. With most herbs, however, this term is used in the wider sense for a remedy that effects the female reproductive system.

Hepatic: Hepatics tone and strengthen the liver, and in some cases increase the flow of bile. In a broad holistic approach, they are of great importance because of the fundamental role of the liver in maintaining health by facilitating digestion and removing toxins from the body.

Laxative: These are plants that promote bowel movement. They are divided into those that work by providing bulk, those that stimulate the production of bile in the liver and its release from the gallbladder, and those that directly trigger peristalsis (wave-like contractions of the smooth muscles of the digestive tract).

Nervine: Nervines help the nervous system and can be subdivided into three groups. Nervine tonics strengthen and restore the nervous system. Nervine relaxants ease anxiety and tension. Nervine stimulants directly stimulate nerve activity.

Stimulating: Stimulants quicken and invigorate the physiological and metabolic activity of the body.

Tonic: Tonics nurture and enliven, i.e., make vigorous or active.

The above information was obtained from Alternative Medicine, compiled by the Burton Goldberg Group and published by Future Medicine Publishing (1993), incorporated herein by reference.

Information contained herein was also obtained from portions of the following texts, all of which are incorporated herein by reference: *Therapeutic Herbalism*, A correspondence course in Phytotherapy, by David L. Hoffmann; *CRC Handbook of Medicinal Herbs*, James A. Duke, Ph.D. author, CRC Press, Inc. (1985); and *British Herbal Compendium*, edited by Peter R. Bradley, British Herbal Medicine Association (Vol. 1).

The present invention is directed to an herbal compound which aids in the relief of symptoms caused by female hormonal imbalances.

In the preferred embodiment, the herbal compound of the present invention comprises red raspberry, bayberry, blue cohosh, capsicum, cascara sagrada, damiana, ginger, valerian and a binding agent.

Red raspberry (*Rubus Occidentalis L.*), part of the rosaceae family, is adaptogenic, alterative, antispasmodic, emmenagogue, stimulant and tonic. In the preferred embodiment, the root, leaves and fruit are used. The physiological effects of red raspberry leaves are reported to include use as a smooth muscle and uterine muscle relaxant, as well as a virus inhibitor. Red raspberry contains vitamins A, B, C, D and E, as well as iron, phosphorous, magnesium and calcium.

Bayberry (*Myrica pensylvanica Loisel*), part of the myricaceae family, is an astringent, adaptogenic, alterative, circulatory stimulant and tonic. In the preferred embodiment, the leaves, bark and fruit are used. Bayberry acts to complement the other herbs, and is used to stimulate the system to boost vitality and resistance, and aids the process of digestion, blood-making and nutrition. Bayberry contains a high level of vitamin C.

Blue cohosh (*Caulophylum thalictroides*), part of the berberidaceae family, is a diuretic, emmenagogue, nervine, and uterine anti-spasmodic. In the preferred embodiment, the root is used. Blue cohosh is used to relieve the pain that accompanies menstruation by easing uterine cramps, as well as menopausal pain, restlessness and discomfort. Blue cohosh is also used to relieve irregular menstruation, dull frontal headaches, as a nervine relaxant, as well as to relieve vaginitis. Blue cohosh contains vitamins E and B-complex, and calcium, magnesium, phosphorous and potassium.

Capsicum, also known as capsaicin (*Capsicum minimum, Capsicum annuum L.*), part of the solanaceae family, is alterative, stimulating and a tonic. In the preferred embodiment, the fruit is used. Capsicum stimulates blood flow, promotes sound sleep and aids in digestion. Capsicum, known as a "supreme and harmless internal disinfectant", increases the power of the other herbs by acting as a catalyst therefor, quickly carrying all other herbs to the part of the body where needed most, thereby acting to increase their effectiveness. Capsicum is high in vitamin A, B-complex, C, iron and calcium, and also contains magnesium, phosphorus, sulfa and potassium.

Cascara sagrada (Rhamnus Caroliniana Walt, *Rhamni purshiani cortex*), part of the rhamnaceae family, is alterative, bitter and a tonic. In the preferred embodiment, the bark is used. Cascara sagrada is rich in hormone-like oils and is used as a laxative to alleviate chronic constipation. Cascara sagrada contains B-complex, calcium, potassium and magnesium.

Damiana, also known as turnera (*Turnera aphrodisiaca UrB*), part of the turneraceae family, is adaptogenic, alterative, mild laxative, nervine and stimulant. In the preferred embodiment, the leaves are used. Damiana is used for its tonic action on the central nervous and hormonal system, to relieve anxiety, depression, headaches during menstruation and exhaustion. Damiana also helps to balance female hormone levels and control hot flashes.

Ginger (Asarum Canadense L., *Zingiber officinale*), part of the zingiberaceae family, is antispasmodic, carminative, diaphoretic, emmenagogue, rubefacient and stimulant. In the preferred embodiment, the root is used. Ginger diminishes headaches, uterine pain from any cause at the menstrual epoch and other general aches and pains, stimulates peripheral circulation, aids in digestion, and has anti-oxidant and anti-microbial effects. Ginger contains vitamins A, B-complex and C, and calcium, phosphorous, iron, sodium, potassium and magnesium.

Valerian (*Valeriana officinalis* L.), part of the valerian family, is an antispasmodic, calmative, emmenagogue and nerve tonic. In the preferred embodiment, the root is used. Valerian is used for nervousness, anxiety, insomnia, headaches, irritability and intestinal cramps. Valerian acts as a sedative when agitation is present as a stimulant when fatigue is present, is antibacterial and liver-protective.

In the preferred embodiment, the herbs are grown outdoors. When harvested, the herbs are preferably gassed to kill bugs and eggs, and then air dried. Most importantly, only those herbs having certificates of safety and purity from the growers, as recognized by the U.S. Food and Drag Administration, are preferably used.

The above herbs are preferably pulverized and cold-compressed, and used in the herbal compound of the present invention. The herbal compound of the present invention was successfully produced by the formula presented in Example 1, as follows:

EXAMPLE 1

| Herbal Constituent | Weight (in milligrams) |
| --- | --- |
| red raspberry | 36 |
| bayberry | 18 |
| blue cohosh | 18 |
| capsicum | 18 |
| cascara sagrada | 18 |
| damiana | 18 |
| ginger | 18 |
| valerian | 18 |
| total | 162 |

The above herbal compound is preferably produced as a tablet for easy intake. In the preferred embodiment, the herbal constituents are formed in a tablet and bound together via a binding agent. The binding agent was successfully produced by the formula presented in Example 2, as follows:

EXAMPLE 2

| Binding Agent Constituent | Weight (in milligrams) |
| --- | --- |
| cellulose | 25.00 |
| vegetable powder | 9.52 |
| duratex stearic acid | 9.52 |
| di-calcium phosphate (DCP) | 6.80 |
| silica | 6.67 |
| magnesium stearate | 6.67 |

The binding agent preferably binds the pulverized herbal compound together. Cellulose is preferably used to hold the compressed tablet together, while vegetable powder is preferably used as a food carrier so that the herbal compound can safely and effectively be taken on an empty stomach. The other constituents of the binding agent are preferably used to allow the tablet to dissolve in the stomach, rather than in the intestine.

The tablet is preferably also coated with food glaze.

Although illustrative embodiments of the present invention have been described in detail with reference to the accompanying drawings, it is to be understood that the invention is not limited to those precise embodiments. Various changes or modifications may be effected therein by one skilled in the art without departing from the scope or spirit of the invention.

What I claim as my invention is:

1. An herbal composition comprising:

red raspberry;

bayberry;

blue cohosh;

capsicum;

cascara sagrada;

damiana;

ginger; and valerian.

2. The herbal composition of claim 1, wherein the ratio of red raspberry to the ratio of the other herbal components is about two to one.

3. The herbal composition of claim 1, said herbal composition further comprising a binding agent.

4. The herbal composition of claim 3, wherein said binding agent comprises cellulose.

5. The herbal composition of claim 3, wherein said binding agent comprises vegetable powder.

6. The herbal composition of claim 3, wherein said binding agent allows the herbal composition to dissolve in the stomach.

7. The herbal composition of claim 3, wherein said herbal composition is formed in a predetermined shape having an exterior surface, and wherein the exterior surface of said shape is coated with a food glaze.

* * * * *